July 5, 1966 H. C. SWIM ETAL Plant Pat. 2,649
ROSE PLANT
Filed Aug. 10, 1965
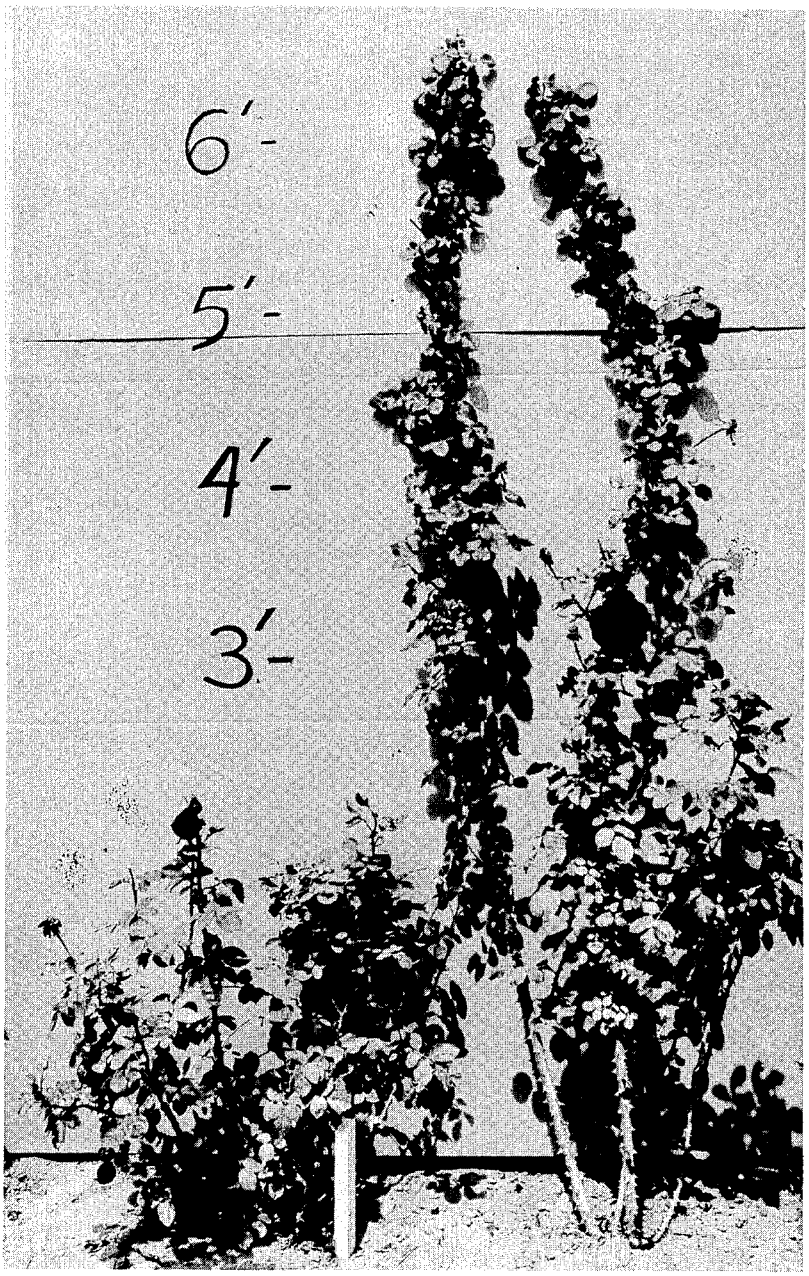
PARENT
Inventors
H. C. Swim
O. L. Weeks
By: Robb & Robb
Attorneys United States Patent Office Plant Pat. 2,649
Patented July 5, 1966

2,649
ROSE PLANT

Herbert C. Swim, Ontario, and O. L. Weeks, Chino, Calif., assignors to O. L. Weeks, doing business as Weeks Wholesale Rose Grower, Chino, Calif.

Filed Aug. 10, 1965, Ser. No. 478,779
1 Claim. (Cl. Plt.—6)

The present invention relates to a new and distinct variety of rose plant of the climber class, which was discovered by us as a sport of the variety known as "Oklahoma" (Plant Patent No. 2,326).

At the time of our discovery aforesaid, we were inspecting test plants of our variety "Oklahoma" being grown in test gardens at Ontario, California. In the course of our inspection, we noticed that one plant of the "Oklahoma" group exhibited an unusual habit of growth, and upon closer inspection thereof, we found that it had sported and produced a climbing cane. We thereupon took immediate steps to preserve the sport and to asexually reproduce the same by budding in the regular growing fields of our assignee at Chino, California. Continued observations of the asexual reproductions conclusively established that the new sport was substantially identical with the parent variety "Oklahoma" except for the climbing habit aforementioned, combined with a habit of bearing flowers of larger than average size as compared with the flowers of "Oklahoma" which are otherwise indistinguishable, and the further distinguishing habit that the major portion of the flowers of the new sport are borne in the spring season and the flowers are produced on stems that grow as laterals from the climbing canes as distinguished from the flowers of "Oklahoma" which are usually produced throughout the growing season but on no particular place on the bush and in no set pattern.

All of these distinguishing features and characteristics of the new sport are fixed and transmissible by asexual reproduction, and so far as we know, the variety "Oklahoma," which is a regular bush type of rose plant, has never previously exhibited a climbing habit of growth, and we are convinced that our new sport is definitely a new and distinct variety.

Being substantially identical with the parent variety in all other respects, except for the climbing habit which is evidenced by long, strong canes which attain a mature height of at least seven feet or more, larger flower size, averaging about five to six and one-half inches in diameter in the fully open flowers, and the lateral flower bearing and spring production habits as aforementioned, it is unnecessary to specifically describe our new sport in detail herein. It otherwise substantially conforms to the detailed description embodied in Plant Patent No. 2,326, issued December 17, 1963, to which reference may be readily had.

For convenience, the accompanying drawing is presented to illustrate the climbing habit of growth of the new sport, in comparison with the typical bush habit of a specimen plant of the parent variety "Oklahoma."

We claim:

A new and distinct variety of rose plant of the climber class, substantially as herein shown and described, characterized particularly as to novelty by being substantially identical with its parent variety "Oklahoma" (Plant Patent No. 2,326) except for its climbing habit of growth, substantially larger than average flower size, and a habit of bearing the major portion of its flowers in the spring and on stems which grow as laterals from the climbing canes.

No references cited.

ABRAHAM G. STONE, *Primary Examiner.*